(12) United States Patent
Arai

(10) Patent No.: US 7,268,106 B2
(45) Date of Patent: Sep. 11, 2007

(54) AQUEOUS LIQUID DETERGENT COMPOSITION

(75) Inventor: Kenji Arai, Tokyo (JP)

(73) Assignee: Kao Corporation, Tokyo (JP)

( * ) Notice: Subject to any disclaimer, the term of this patent is extended or adjusted under 35 U.S.C. 154(b) by 416 days.

(21) Appl. No.: 10/733,245

(22) Filed: Dec. 12, 2003

(65) Prior Publication Data

US 2004/0162229 A1    Aug. 19, 2004

(51) Int. Cl.
*A61K 7/06* (2006.01)
*A61K 31/08* (2006.01)
*C11D 1/29* (2006.01)

(52) U.S. Cl. .................. 510/130; 510/136; 510/156; 510/505; 510/506; 510/421; 424/70.1; 424/401; 514/723; 252/121; 252/551

(58) Field of Classification Search ............... 252/89.1, 252/142, 121, 551; 424/70.12, 401, 70.1; 510/122, 123, 125, 128, 130, 136, 156, 421, 510/505, 506; 514/723
See application file for complete search history.

(56) References Cited

U.S. PATENT DOCUMENTS

| RE34,584 E | * | 4/1994 | Grote et al. ................. 252/142 |
| 5,466,395 A | | 11/1995 | Tosaka et al. |
| 5,911,979 A | * | 6/1999 | Midha et al. ............ 424/70.12 |
| 6,165,955 A | * | 12/2000 | Chen et al. ................. 510/123 |
| 6,417,146 B1 | | 7/2002 | Miyajima et al. |

FOREIGN PATENT DOCUMENTS

| JP | 06157292 A | * | 11/1992 |
| JP | 6-17088 | | 1/1994 |
| JP | 6-17095 | | 1/1994 |
| JP | 06293629 A | * | 10/1994 |
| JP | 06293630 A | * | 10/1994 |
| JP | 11-49639 | | 2/1999 |
| JP | 2001-114652 | | 4/2001 |

* cited by examiner

*Primary Examiner*—Douglas McGinty
*Assistant Examiner*—Preeti Kumar
(74) *Attorney, Agent, or Firm*—Oblon, Spivak, McClelland, Maier & Neustadt, P.C.

(57) ABSTRACT

Provided is an aqueous liquid detergent composition containing a long-chain fatty acid glycol ester represented by the following formula (1):

$$R^1COO(CH_2CH_2O)_mA \quad (1)$$

wherein, A is H or $COR^2$, $R^1$ and $R^2$ represents a $C_{11-21}$ alkyl or alkenyl group, and m stands for a number of from 1 to 3, and a surfactant, wherein the fatty acid constituent of the long-chain fatty acid glycol ester contains 60 wt. % or greater of fatty acids having 18 or more carbon atoms, 40 wt. % or less of a fatty acid having 16 carbon atoms, and 5 wt. % or less of fatty acids having less than 16 carbon atoms; and the composition has a pH of from 1 to 5 at 25° C. when diluted to 20 times the weight with water.

The detergent composition has benefits such as an elegant and expensive-looking pearl luster, is excellent in stability of a pearling agent, particularly long storage stability at high temperatures, and has good detergency and foaming property.

17 Claims, No Drawings

AQUEOUS LIQUID DETERGENT COMPOSITION

FIELD OF THE INVENTION

The present invention relates to an aqueous liquid detergent composition having a pearling agent.

BACKGROUND OF THE INVENTION

Detergents have hitherto been developed with a view to attaining improvement both in cleaning function and in imparting conditioning effects and mildness. With diversification of lifestyles, needs of consumers are becoming more diverse than in the past. Accordingly, consumers request detergents having various appearances or various functions.

With regards to the appearance, a pearlescent appearance is given to detergents in order to make them look luxurious and make consumers feel rich, while with regards to the function, detergents are requested to have not only detergency, but also, in the case of a shampoo, various functions capable of providing hair with a soft feel, manageability, easy combing property and the like.

Alkylene glycol mono- or di-alkyl esters are known as a pearling substance. Their alkyl chain length however differs widely, owing to the raw materials used so therefore the desired pearlescent appearance cannot be attained readily. For the purpose of imparting hair with a soft feel, manageability, or easy combing property, it is known to make the pH of a detergent acidic, which however leads to the decomposition of the ester of the pearling agent, whereby causing separation and impairment of the pearlescent appearance to seriously damage the stability of the composition.

SUMMARY OF THE INVENTION

In one aspect of the present invention, there is thus provided an aqueous liquid detergent composition containing a long-chain fatty acid glycol ester represented by the following formula (1):

$$R^1COO(CH_2CH_2O) \quad (1)$$

wherein, $R^1$ represents a $C_{11-21}$ alkyl or alkenyl group, A represents a hydrogen atom or $COR^2$ (in which $R^2$ represents a $C_{11-21}$ alkyl or alkenyl group), and m stands for a number of from 1 to 3, and a surfactant, wherein the fatty acid constituent of the long-chain fatty acid glycol ester contains 60 wt. % or greater of fatty acids having 18 or more carbon atoms, 40 wt. % of fatty acids having 16 carbon atoms, and 5 wt. % or less of fatty acids having less than 16 carbon atoms; and the composition has a pH of from 1 to 5 at 25° C. when diluted to 20 times the weight with water.

In another aspect of the present invention, there is also provided an aqueous liquid detergent composition containing a long-chain fatty acid glycol ester represented by the above-described formula (1) and a surfactant, wherein the fatty acid constituent of the long-chain fatty acid glycol ester contains 65 to 85 wt. % of fatty acids having 18 or more carbon atoms, 15 to 35 wt. % of fatty acids having less than 18 carbon atoms, 35 wt. % or less of fatty acids having 16 carbon atoms, and 5 wt. % or less of fatty acids having less than 16 carbon atoms; and the composition has a pH of from 1 to 5 at 25° C. when diluted to 20 times the weight with water.

DETAILED DESCRIPTION OF THE INVENTION

The present invention relates to an acid detergent composition in which a pearling agent contained therein is stable.

The present inventors have found that an acid detergent composition excellent in pearlescent appearance and in stability of a pearling agent (particularly, long-term storage stability at high temperatures), and capable of maintaining good detergency and foaming properties even after long term storage can be obtained by controlling the distribution of the alkyl chain length of the alkylene glycol mono- or di-alkyl ester serving as a pearling agent within a predetermined range.

In the long-chain fatty acid glycol ester (1) which serves as a pearling agent, the alkyl group or alkenyl group represented by $R^1$ or $R^2$ in formula (1) has 11 to 21 carbon atoms, preferably 17 to 21 carbon atoms, more preferably 17 carbon atoms. $R^1$ and $R^2$ are preferably a linear alkyl group. The long-chain fatty acid glycol ester (1) may exist as a mixture or the fatty acid component and may contain various fatty acids different in the number of carbon atoms. However, the distribution of the number of carbon atoms in the fatty acids is preferably as narrow as possible. Specifically, the fatty acid constituent of the long-chain fatty acid glycol ester (1) contains 60 wt. % or greater of fatty acids having 18 or more carbon atoms, 40 wt. % or less of fatty acids having 16 carbon atoms, and 5 wt. % or less of fatty acids having less than 16 carbon atoms; and preferably contains of 65 to 85 wt. % of fatty acids having 18 or more carbon atoms, 15 to 35 wt. % of fatty acids having less than 18 carbon atoms, 35 wt. % or less of fatty acids having 16 carbon atoms, and 5 wt. % or less of fatty acids having less than 16 carbon atoms.

Specific preferred examples of the long-chain fatty acid glycol ester of formula (1) include ethylene glycol mono-fatty acid esters, ethylene glycol di-fatty acid esters, triethylene glycol mono-fatty acid esters and triethylene glycol di-fatty acid esters, of which ethylene glycol di-fatty acid esters are preferred.

The long-chain fatty acid glycol ester of formula (1) is preferably contained in the detergent composition of the present invention in an amount of from 0.3 to 10 wt. %, more preferably from 0.5 to 5 wt. %, and even more preferably from 0.8 to 3 wt. %, from the viewpoints of beautiful pearl luster and good stability (particularly, stability at high temperatures).

In the present invention, anionic surfactants, amphoteric surfactants and nonionic surfactants can be used as the surfactant.

As the anionic surfactants, sulfuric acid, sulfonic acid and carboxylic acid surfactants are preferred. Examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, and higher fatty acid salts. Of these, preferred are polyoxyalkylene alkyl ether sulfates and alkyl sulfates, and more preferred are those represented by the following formula (2) or (3):

$$R^3O(CH_2CH_2O)_nSO_3M \quad (2)$$

$$R^4OSO_3M \quad (3)$$

wherein, $R^3$ represents a $C_{10-18}$ alkyl or alkenyl group, $R^4$ represents a $C_{10-18}$ alkyl group, M represents an alkali metal, alkaline earth metal, ammonium, alkanolamine or basic amino acid, and n is a weight average number of from 1 to 5.

Examples of the amphoteric surfactants include acetic acid betaines, amidoacetic acid betaines, sulfobetaines, amidosulfobetaines, phosphobetaines, alkylamine oxides, and amidoamine oxides. Of these, fatty acid amidopropylbetaines such as cocamidopropyl betaine and lauramidopropyl betaine are preferred.

Examples of the nonionic surfactant include polyoxyalkylene alkyl ethers, polyoxyalkylene fatty acid esters, polyoxyalkylene sorbitan esters, polyoxyalkylene sorbitan fatty acid esters, polyoxyalkylene sorbitol fatty acid esters, polyoxyalkylene glycerin fatty acid esters, monoglycerides, sorbitan fatty acid esters, fatty acid monoethanolamides, fatty acid diethanolamides and alkyl polyglucosides.

Two or more of these surfactants may be used in combination. The surfactant is preferably contained in an amount of from 10 to 50 wt. %, more preferably from 10 to 30 wt. %, even more preferably from 10 to 20 wt. % based on the detergent composition of the present invention, from the viewpoints of foaming property, liquid properties during use and detergency.

The detergent composition of the present invention has a pH at 25° C. of from 1 to 5, preferably from 3 to 4 when diluted to 20 times the weight with water. For the pH adjustment, an organic or inorganic acid, and if necessary a base are used. Examples of the organic acid include hydroxyl acids, monocarboxylic acids, dicarboxylic acids, tricarboxylic acids, polycarboxylic acids, alkylsulfuric acids, and alkylphosphoric acids. The hydroxyl acids include glycolic acid, lactic acid, oxybutyric acid, glyceric acid, malic acid and tartaric acid; the monocarboxylic acids include acetic acid; the dicarboxylic acids include malonic acid, succinic acid, glutamic acid, adipic acid, maleic acid, fumaric acid and phthalic acid; and the tricarboxylic acids include citric acid. Examples of the inorganic acid include hydrochloric acid, sulfuric acid and phosphoric acid. Of these, organic acids are preferred, of which α-hydroxycarboxylic acids are more preferred, and lactic acid and malic acid are even more preferred, because these acids can give the hair excellent luster, flexibility and manageability. Examples of the base include sodium hydroxide and potassium hydroxide. The organic acid or inorganic acid is contained preferably in an amount of from 0.05 to 10 wt. %, more preferably from 0.1 to 5 wt. %, even more preferably from 0.5 to 1 wt. % based on the detergent composition of the present invention.

The detergent composition of the present invention may contain silicones for further improvement in the conditioning effects. The silicones include dimethylpolysiloxanes (viscosity: 5 mm$^2$/s to 20 million mm$^2$/s), amino-modified silicones, polyether-modified silicones, methylphenylpolysiloxanes, fatty acid-modified silicones, alcohol-modified silicones, alkoxy-modified silicones, epoxy-modified silicones, fluorine-modified silicones, cyclic silicones and alkyl-modified silicones, of which dimethylpolysiloxanes are preferred. The content of the silicone in the detergent composition of the present invention is preferably from 0.01 to 10 wt. %. The detergent composition of the present invention may contain other conditioning components such as a cationic polymer (cationic cellulose, cationic guar gum, or the like). Their content in the detergent composition of the present invention is preferably from 0.1 to 5 wt. %.

The detergent composition of the present invention may contain, in addition, components employed ordinarily for detergent compositions according to the intended use. Examples of such components include humectants such as propylene glycol, glycerin, diethylene glycol monoethyl ether, sorbitol and panthenol; colorants such as dyes and pigments; viscosity regulators such as methyl cellulose, polyethylene glycol and ethanol; plant extracts; antiseptics; bactericides; chelating agents; vitamin preparations; anti-inflammatory agents; perfumes; ultraviolet absorbers; and antioxidants.

The detergent composition of the present invention can be used as cleansing agents for the human body such as shampoo, body soap and face wash.

EXAMPLES

Example 1

Shampoos having the composition shown in Table 1 were prepared and their appearance was evaluated in accordance with the below-described criteria.

Criteria for Evaluation

Elegance of Appearance

Appearance was evaluated by a panel of 5 experts based on the below-described criteria:

A: At least 4 out of 5 experts feel that it has an elegant appearance.

B: 2 to 3 out of 5 experts feel that it has an elegant appearance.

C: 1 or less out of 5 experts feels that it has an elegant appearance.

Precipitation of Pearling Agent After Storage

The shampoo was stored in a glass bottle at 25° C. for 20 days and precipitation of the pearling agent was observed.

A: Precipitation is not observed.

B: Precipitation is observed.

Stability Under Acid Conditions

The pearlescent suspension (shampoo) was stored at 50° C. and the period of time during which the stability (pearlescent appearance) of the system was maintained was observed and evaluated.

A: stable for 1 month or longer.

B: stable for 20 days

C: Pearlescent appearance disappears before storage term reaches 20 days.

Elegance of Appearance After Storage

After storage at 50° C. for 20 days, the appearance was evaluated by a panel of 5 experts in accordance with the below-described criteria:

A: At least 4 out of 5 experts feel it has an elegant appearance.

B: 2 to 3 out of 5 experts feel it has an elegant appearance.

C: 1 or less out of 5 experts feels it has an elegant appearance.

TABLE 1

| (wt. %) | Example 1 | Example 2 | Example 3 | Example 4 | Example 5 | Example 6 | Comp. Ex. 1 | Comp. Ex. 2 |
|---|---|---|---|---|---|---|---|---|
| Ethylene glycol di($C_{18}$ fatty acid) ester | 1.485 | 1.485 | 1.485 | 1.2 | 1.2 | 1.2 | 0.98 | 0.98 |
| Ethylene glycol di($C_{22}$ fatty acid) ester | — | — | — | 0.1 | 0.1 | 0.1 | — | — |
| Ethylene glycol di($C_{16}$ fatty acid) ester | 0.495 | 0.495 | 0.495 | 0.5 | 0.5 | 0.5 | 0.98 | 0.98 |
| Ethylene glycol mono($C_{16}$ fatty acid) ester | 0.005 | 0.005 | 0.005 | 0.05 | 0.05 | 0.05 | 0.02 | 0.02 |
| Ethylene glycol mono(C18 fatty acid) ester | 0.015 | 0.015 | 0.015 | 0.12 | 0.12 | 0.12 | 0.02 | 0.02 |
| Ethylene glycol mono($C_{22}$ fatty acid) ester | — | — | — | 0.01 | 0.01 | 0.01 | — | — |
| [Ratio of fatty acids having at least 18 carbon atoms] | 0.75 | 0.75 | 0.75 | 0.72 | 0.72 | 0.72 | 0.50 | 0.50 |
| [Ratio of a fatty acid having 16 carbon atoms] | 0.25 | 0.25 | 0.25 | 0.28 | 0.28 | 0.28 | 0.50 | 0.50 |
| [Ratio of fatty acids having less than 16 carbon atoms] | 0 | 0 | 0 | 0 | 0 | 0 | 0 | 0 |
| Sodium polyoxyethylene (2.0) sulfate | 15 | — | — | 15 | — | — | 15 | — |
| Sodium polyoxyethylene (3.0) sulfate | — | 15 | — | — | 15 | — | — | 15 |
| Sodium polyoxyethylene (1.5) sulfate | — | — | 15 | — | — | 15 | — | — |
| Cocamidopropyl betaine | 2 | — | 0.5 | 2 | — | 0.5 | 2 | — |
| Lauramidopropyl betaine | — | 1 | 0.3 | — | 1 | 0.3 | — | 1 |
| Amodimethicone | — | — | 0.2 | — | — | 0.2 | — | — |
| Dimethylpolysiloxane (10 $mm^2/s$ at 25° C.) | 1.5 | 1 | — | 1.5 | 1 | — | 1.5 | 1 |
| Dimethylpolysiloxane (500 $mm^2/s$ at 25° C.) | — | 0.5 | — | — | 0.5 | — | — | 0.5 |
| Dimethylpolysiloxane (10000 $mm^2/s$ at 25° C.) | 0.1 | 2 | — | 0.1 | 2 | — | 0.1 | 2 |
| Dimethylpolysiloxane (10 million $mm^2/s$ at 25° C.) | 0.5 | — | 2 | 0.5 | — | 2 | 0.5 | — |
| Cationic cellulose ("Catinal LC-10" product of Toho Chemical) | 0.5 | 0.5 | 0.2 | 0.5 | 0.5 | 0.2 | 0.5 | 0.5 |
| Cationic guar gum ("Rabole gum CG-M", product of Dainippon Pharmaceutical) | — | — | 0.5 | — | — | 0.5 | — | — |
| Cationic polymer ("Merquat 2001", product of CALGON) | — | 1 | — | — | 1 | — | — | 1 |
| Cationic polymer ("Merquat 550", product of CALGON) | 0.5 | — | 1 | 0.5 | — | 1 | 0.5 | — |
| Benzoic acid | 0.3 | 0.5 | — | 0.3 | 0.5 | — | 0.3 | 0.5 |
| Sodium chloride | — | 0.1 | 0.1 | — | 0.1 | 0.1 | — | 0.1 |
| Lactic acid | 2 | — | — | 2 | — | — | 2 | — |
| Citric acid | — | 1.5 | — | — | 1.5 | — | — | 1.5 |
| Malic acid | — | — | 0.7 | — | — | 0.7 | — | — |
| pH regulator (hydrochloric acid/sodium hydroxide) | q.s. | q.s. | q.s. | q.s. | q.s. | q.s. | q.s. | q.s. |
| [pH; when diluted to 20 times the weight with water, 25° C.] | 3 | 4 | 4.5 | 3 | 4 | 4.5 | 3 | 4 |
| Evaluation  Elegance of appearance | A | A | A | A | A | A | C | C |
| Precipitation of pearling agent after storage | A | A | A | A | A | A | A | A |
| Stability under acidic conditions | A | A | A | A | A | A | C | C |
| Elegance of appearance after storage | A | A | A | A | A | A | C | C |

The invention claimed is:

1. An aqueous liquid detergent composition comprising:
a plurality of long-chain fatty acid glycol esters represented by the following formula (1):

$$R^1COO(CH_2CH_2O)_mA \quad (1)$$

wherein, $R^1$ represents a $C_{11-21}$ alkyl or alkenyl group, A represents a hydrogen atom or $COR^2$ (in which $R^2$ represents a $C_{11-21}$ alkyl or alkenyl group), and m stands for a number of from 1 to 3; and a surfactant, wherein the fatty acid constituent of the long-chain fatty acid glycol ester contains 65 to 85 wt. % of fatty acids having 18 or more carbon atoms, 15 to 35 wt. % of fatty acids having less than 18 carbon atoms, 35 wt. % or less of fatty acids having 16 carbon atoms, and 5 wt. % or less of fatty acids having less than 16 carbon atoms; and wherein the composition has a pH of from 1 to 5 at 25° C. when diluted to 20 times the weight with water.

2. The composition according to claim 1, wherein the long-chain fatty acid glycol esters of formula (1) comprise a glycol ester selected from the group consisting of ethylene glycol mono-fatty acid esters, ethylene glycol di-fatty acid esters, triethylene glycol mono-fatty acid esters, triethylene glycol di-fatty acid esters, and mixtures thereof.

3. The composition according to claim 1, comprising from 0.3% to 10 wt. % of the long-chain fatty acid glycol ester of formula (1).

4. The composition according to claim 1, wherein the surfactant is selected from the group consisting of amphoteric surfactants, nonionic surfactants, and mixtures thereof.

5. The composition according to claim 4, comprising from 10 to 50 wt. % of the surfactant.

6. The composition according to claim 1, further comprising from 0.05% to 10 wt. % of an organic acid or inorganic acid.

7. The composition according to claim 2, wherein the long-chain fatty acid glycol ester of formula (1) is an ethylene glycol di-fatty acid ester.

8. The composition according to claim 1, further comprising a silicone selected from the group consisting of dimethylpolysiloxanes, amino-modified silicones, polyether-modified silicones, methylphenylpolysiloxanes, fatty acid-modified silicones, alcohol-modified silicones, alkoxy-modified silicones, epoxy-modified silicones, fluorine-modified silicones, cyclic silicones, alkyl-modified silicones, and mixtures thereof.

9. The composition according to claim 8, comprising from 0.01 to 10 wt. % of dimethylpolysiloxanes.

10. The composition according to claim 1, comprising from 0.5% to 5 wt. % of the long-chain fatty acid glycol ester of formula (1).

11. The composition according to claim 1, comprising from 0.8% to 3 wt. % of the long-chain fatty acid glycol ester of formula (1).

12. The composition according to claim 4, comprising from 10 to 30 wt. % of the surfactant.

13. The composition according to claim 4, comprising from 10 to 20 wt. % of the surfactant.

14. The composition according to claim 1, wherein the pH is from 3 to 4.

15. A shampoo comprising the aqueous liquid detergent composition according to claim 1.

16. A body soap comprising the aqueous liquid detergent composition according to claim 1.

17. A face wash comprising the aqueous liquid detergent composition according to claim 1.

* * * * *